(12) United States Patent
Taeubert et al.

(10) Patent No.: US 11,058,872 B2
(45) Date of Patent: Jul. 13, 2021

(54) IMPLANTABLE LEAD

(71) Applicant: BIOTRONIK SE & Co. KG, Berlin (DE)

(72) Inventors: Kerstin Taeubert, Berlin (DE); Gernot Kolberg, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 432 days.

(21) Appl. No.: 15/808,217

(22) Filed: Nov. 9, 2017

(65) Prior Publication Data

US 2018/0133464 A1 May 17, 2018

(30) Foreign Application Priority Data

Nov. 15, 2016 (EP) .................................. 16198876

(51) Int. Cl.
*A61N 1/05* (2006.01)

(52) U.S. Cl.
CPC ............ *A61N 1/0573* (2013.01); *A61N 1/057* (2013.01); *A61N 1/0565* (2013.01)

(58) Field of Classification Search
CPC .............. A61N 1/3756; A61N 1/37205; A61F 2220/0075
See application file for complete search history.

(56) References Cited

U.S. PATENT DOCUMENTS

| 5,456,708 | A | * | 10/1995 | Doan | A61N 1/056 607/127 |
| 9,302,098 | B2 | | 4/2016 | Zhang et al. | |
| 2005/0261664 | A1 | * | 11/2005 | Rome | A61M 25/0097 604/508 |
| 2011/0282286 | A1 | * | 11/2011 | Argentine | A61M 39/0606 604/164.13 |
| 2013/0296917 | A1 | * | 11/2013 | Rees | A61B 17/12022 606/200 |
| 2014/0165395 | A1 | * | 6/2014 | Jang | A61N 1/05 29/876 |

* cited by examiner

*Primary Examiner* — Michael J D Abreu
(74) *Attorney, Agent, or Firm* — Buchanan Ingersoll & Rooney PC

(57) ABSTRACT

Implantable lead having an electrode body with a free end and an inner part axially movable or rotatably movable with respect to it and an end on which means of fixation are extendable out of the free end by axially displacing the inner part, the inner periphery of the electrode body having an elastically deformable, peripheral, ring or ring segment-shaped, sealing/resistance element fixed to it. The outer periphery of the inner part having a section whose diameter changes (decreases) in the axial direction; this section passes the sealing/resistance element when the inner part is axially displaced. The inner periphery of the electrode body having a section whose diameter changes (decreases) in the axial direction; this section placed so that the sealing/resistance element passes this section when the inner part is axially displaced, the sealing/resistance element increasingly deformed during axial displacement of the inner part and counteracting movement thereof.

21 Claims, 4 Drawing Sheets

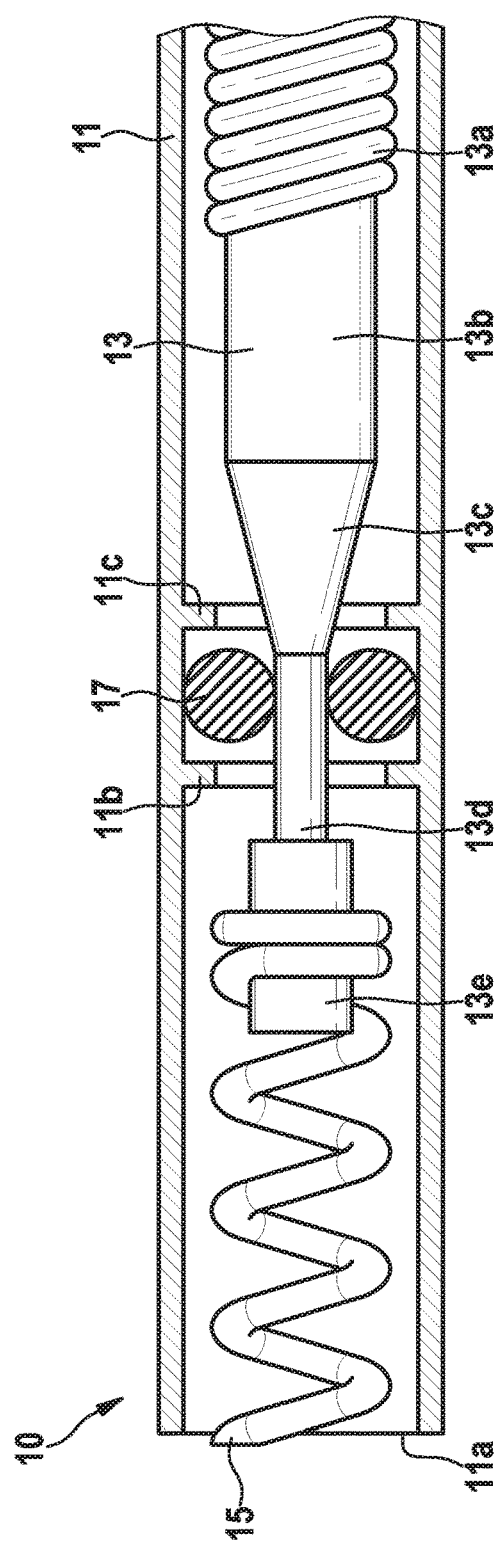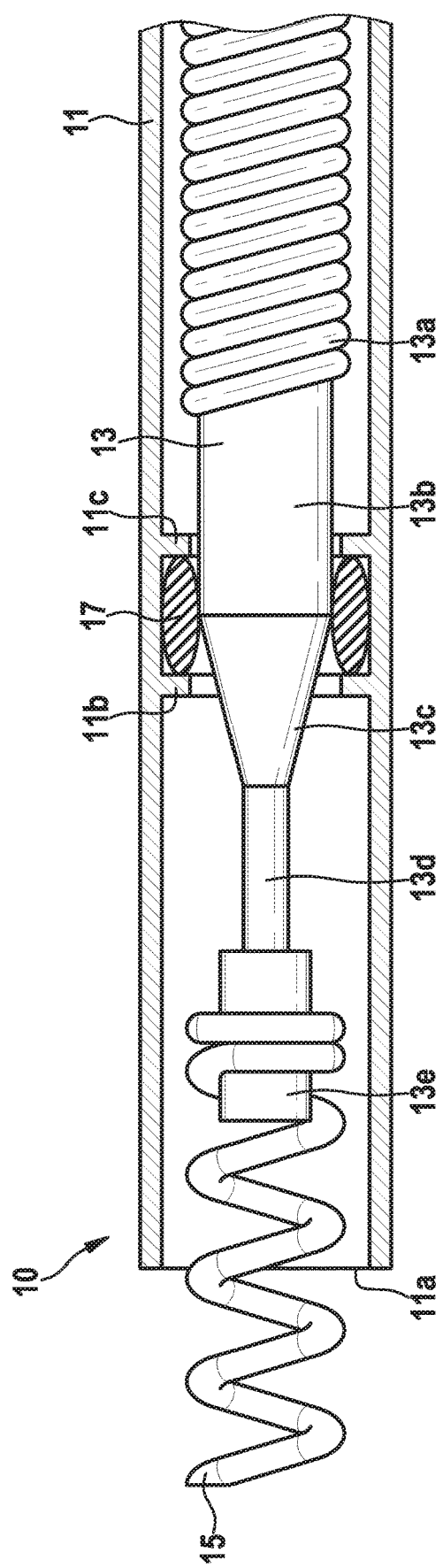

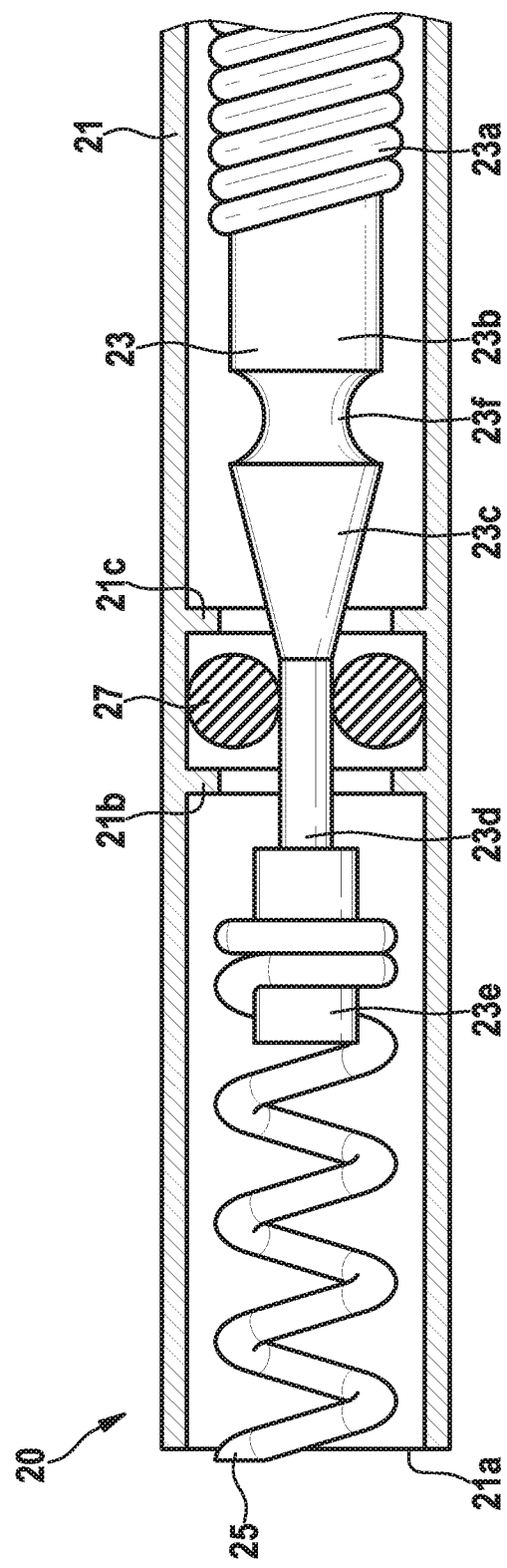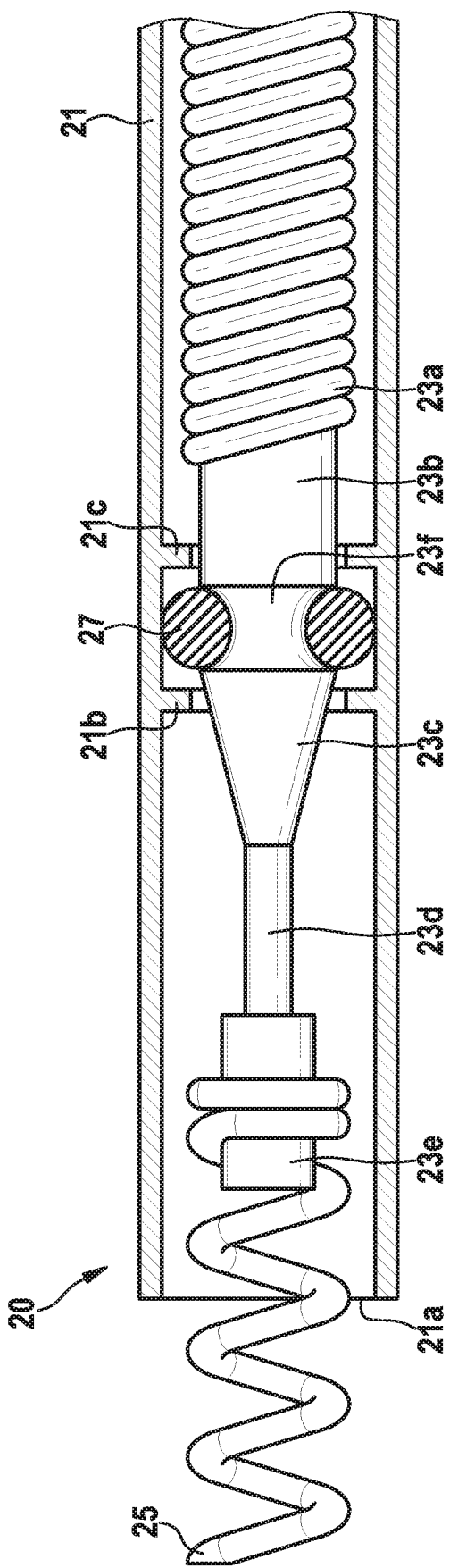
FIG. 2A
FIG. 2B

IMPLANTABLE LEAD

CROSS-REFERENCE TO RELATED APPLICATIONS

This patent application claims the benefit of and priority to co-pending European Patent Application No. EP 16198876.1, filed on Nov. 15, 2016 in the European Patent Office, which is hereby incorporated by reference in its entirety.

BACKGROUND OF THE INVENTION

Field of the Invention

The present invention relates to an implantable lead that has an electrode body with a free end and, arranged in the electrode body, an inner part that is axially movable with respect to it and that has, adjacent to the free end of the electrode body, an end on which there are means of fixation that can be extended out of the free end of the electrode body by axially displacing the inner part, these means of fixation being intended to fix the lead to body tissues in the implanted state.

Description of the Related Art

Such leads have long been known and widely used in clinical practice, especially in the form of electrode leads of pacemaker or cardioverter arrangements. This is due to the substantial advantages of this type of lead, such as, for instance, the especially secure fixation to the cardiac tissue to be stimulated and the resulting high reliability of the entire arrangement, and the relatively simple construction and good handling characteristics for the operating surgeon. A lead type that is especially widespread is that in which the means of fixation are in the form of a helical screw which can exit from the end of the lead and simultaneously be screwed into the cardiac tissue against which it is pressed and, if repositioning is required, can also be unscrewed, with reversed direction of rotation, from the cardiac tissue and pulled back into the end of the lead. Purely as an example of this prior art, please refer to the current U.S. Pat. No. 9,302,098.

Nevertheless, the known leads of this type also have disadvantages. Simple lead constructions with a fixed fixation helix that is, as delivered, already projecting out of the end of the lead, must be covered by a detachable protective covering on the end of the lead during the implantation. The operating surgeon cannot easily calculate the time behavior of these constructions during implantation, and there is a risk of the protective covering detaching too early and problems connected with it when the lead is introduced, as well as a risk of the protective covering detaching too late and the lead being insufficiently fixed as a result.

Therefore, the present invention is directed toward overcoming one or more of the above-mentioned problems and has a goal of making available an improved lead of this type, which should, in particular, be easy to handle, reliably implantable without risk during introduction, and reliable in the long-term use.

BRIEF SUMMARY OF THE INVENTION

At least this is accomplished by an implantable lead with the features of claim 1. Expedient further developments of the inventive idea are the subject of the dependent claims.

The present invention includes the idea of building the lead in such a way that as the distally arranged means of fixation are extended, the ease or difficulty of moving them changes depending on their position with respect to the end of the lead. The inventors think that the extension movement should be very easy in the beginning phase, however, clearly more difficult in the end phase. The fixation, which is initially easy, should, in the screwed-out end state, have its rotatability or axial movability braked or arrested to make unwanted unscrewing more difficult, or to avoid it altogether. Furthermore, the present invention includes the idea of developing an elastically deformable sealing element within the lead that simultaneously functions as a resistance element and is deformed when the means of fixation are screwed out, increasing the resistance counteracting further movement.

Furthermore, the present invention includes the idea that this sealing and/or resistance element is arranged fixed to the inner periphery of the electrode body and that the outer periphery of an inner part that is movable or rotatably movable in the electrode body has a section on it whose diameter changes in axial direction. This section is placed with respect to the position of the sealing and resistance element so that this section passes the peripheral, special ring-shaped or ring segment-shaped sealing and resistance element when the inner part is axially displaced. In an alternative configuration, the sealing and resistance element is arranged on the outer periphery of the inner part (and thus movable with respect to the electrode body), and it is the inner periphery of the electrode body that has a section on it whose diameter changes, this section being positioned so that the sealing and resistance element passes it when the inner part is axially displaced.

In a first application that has special practical importance from the current perspective, the proposed lead is in the form of an electrode lead for connection to an electromedical device, with at least one electrode pole and at least one electrical lead associated with the inner part.

However, use as a catheter lead, that is, without electrode pole(s) and corresponding leads, is also possible in other fields of use than that of electrical stimulation. For example, the proposed lead could also be suitable for correct and reliable positioning of certain sensors for intracorporeal sensing of the parameters of body function, or also for precise local delivery of fluids.

In a design that is preferable from the current perspective, the inner part is held so that it is rotatably movable in the electrode body, in such a way that the means of fixation can be extended out of the free end of the electrode body by superimposed axial displacement and rotation. It is preferable for the inner part to be held in such a way that it is rotatably movable in the electrode body and so that the means of fixation can be extended out of the free end of the electrode body by a screw mechanism. Furthermore, it is preferable for the mentioned screw mechanism to be located at the distal end of the electrode body. In another preferred embodiment, the means of fixation are a helical screw. Preferably, the screw mechanism at the distal end of the electrode body is realized by an advancing element that engages into a helical screw, the helical screw simultaneously being able to function as means of fixation. However, in theory the proposed lead can also be realized with different means of fixation, such as, for instance, with a group of spreadable fixation hooks, or something similar.

In economical and reliably working structural designs, the sealing and resistance element is a ring made of compressible material that is increasingly compressed as the above-mentioned section with changing diameter passes through it while the means of fixation are being extended. The increasing compression can be achieved, for instance, by clamping the compressible ring between two flange rings on its support—that is, the outer electrode body or the inner part—so that the ring cannot "move out" to the side.

In alternative embodiments, a ring (or also a group of ring segments) is provided which is made of an elastically deformable material that is geometrically configured so that the ring is increasingly deformed as the section with changing diameter of the respective lead counterpart passes, and the increase in resistance results from the increasing deformation. These embodiments can also be combined with the previously mentioned ones.

As was already noted above, the sealing and resistance element need not necessarily have the shape of a closed ring but, rather, it can also be formed from a group of ring segments, and the resistance function of this functional element can even be realized, e.g., by individual friction blocks. However, in order to be able to achieve both the resistance element function that is sought in the framework of the present invention and also the sealing element function that is conventionally required, and to do so with small construction expense, the ring shape should be considered preferable, in view of the cylindrical shape of the electrode body and the inner part, which is usually also cylindrically shaped.

In expedient embodiments of the material side of the present invention, the sealing and resistance element has a silicone or polyurethane material. However, other sufficiently compressible and/or elastic biocompatible materials are also suitable.

A further development of the concept the present invention provides that the section of changing diameter on the electrode body or inner part is followed, on at least one side in the axial direction of the lead, by a section of constant diameter whose diameter is equal to the smallest or the largest diameter of the section with changing diameter. Details and advantages of corresponding designs are indicated further below.

Another structural design has, arranged at or near one end of the section with decreasing diameter, a ring-shaped inward-curved section into which the sealing and resistance element slides as the means of fixation are extended and/or pulled back in, partly reversing the deformation of the sealing and resistance element and counteracting further axial movement of the inner part with respect to the electrode body with an abruptly increased resistance. Details about this are also found in the explanations of sample embodiments further below.

In another expedient geometric configuration of the inner part or of the electrode body, the associated section with changing diameter is conically shaped. Alternatively, it can be provided that the section with changing diameter has a surface that tapers in steps or in the form of an arch.

Another embodiment of the present invention provides that the inner part or the electrode body has multiple sections with changing diameter, in particular with diameter that decreases in opposite directions and/or with a different angle of taper.

In other embodiments of the present invention, at least one section of the inner part or the inner wall of the electrode body has a coating on it with a predetermined coefficient of friction with respect to the sealing and resistance element for selective increase or decrease of the resistance counteracting the axial displacement or rotational displacement of the inner part. In one embodiment of this design, various sections of the inner part or the inner wall of the electrode body have coatings on them with different coefficients of friction with respect to the sealing and resistance element.

Further features, aspects, objects, advantages, and possible applications of the present invention will become apparent from a study of the exemplary embodiments and examples described below, in combination with the Figures, and the appended claims.

BRIEF DESCRIPTION OF THE DRAWINGS

The above and other aspects, features and advantages of at least one embodiment of the invention will be more apparent from the following more particular description thereof, presented in conjunction with the following drawings, wherein:

FIGS. 1A and 1B show a schematic longitudinal sections of an implantable lead according to a first embodiment of the invention with its means of fixation pulled back or extended, respectively;

FIGS. 2A and 2B show a schematic longitudinal sections of an implantable lead according to a second embodiment of the invention with its means of fixation pulled back or extended, respectively;

DETAILED DESCRIPTION OF THE INVENTION

Figure 3A:
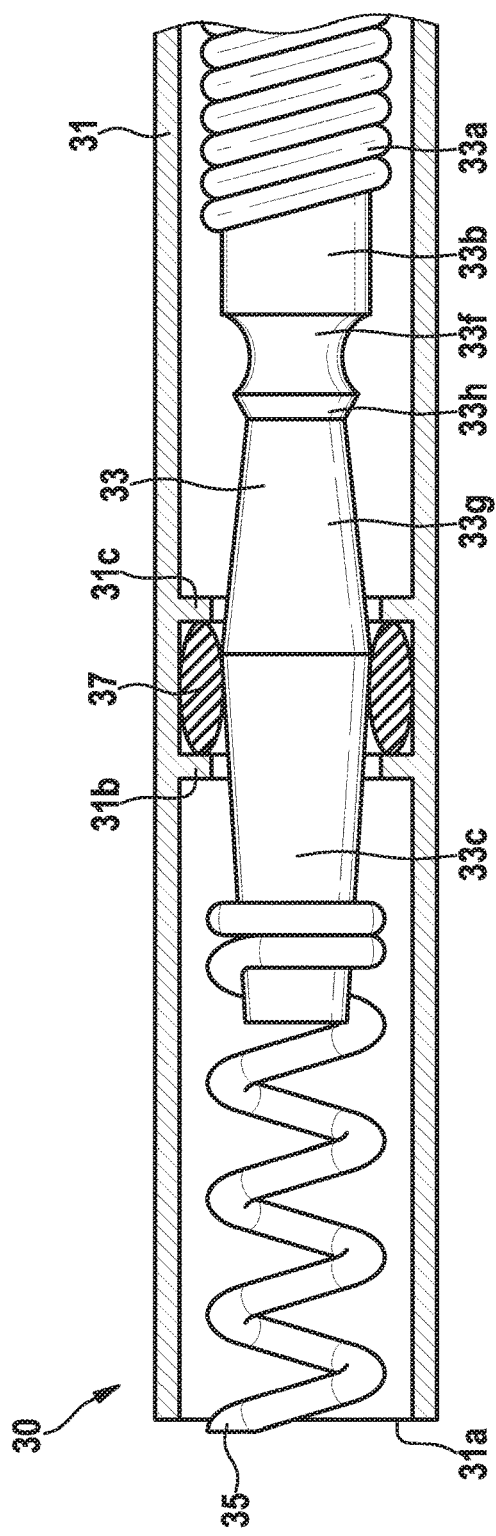
FIGS. 3A and 3B show a schematic longitudinal sections of an implantable lead according to a third embodiment of the invention with its means of fixation pulled back or extended, respectively.

The following description is of the best mode presently contemplated for carrying out at least one embodiment of the present invention. This description is not to be taken in a limiting sense, but is made merely for the purpose of describing the general principles of the present invention. The scope of the present invention should be determined with reference to the claims.

FIGS. 1A and 1B are schematic longitudinal sections showing the distal end section of an implantable electrode lead 10 in which a rotatably movable inner part 13 is arranged in an essentially hollow, cylindrical electrode body 11. The inner part 13 has, on its distal end, which is adjacent to the free (distal) end 11a of the electrode body 11, a helical screw 15 to fix the lead to body tissue, especially cardiac tissue, of a patient. By having the helical screw 15 interact with an advancing element (not shown), it is possible to realize, at the distal end of the electrode body 11, a screw mechanism that axially displaces the rotatably movable inner part 13 by screwing it out. The advancing element can conceivably be, e.g., a pin (not shown), which engages into the helical screw 15, so that the helical screw functions as a screw mechanism.

At a distance from the free end 11a, the inner periphery of the electrode body 11 has two flange rings 11b, 11c formed on it that are spaced apart from one another and that hold a compressible deformable sealing ring 17 between them. The inner part 13 has, in this order in the direction going from proximal to distal, a helical section 13a, a first cylindrical section 13b, a (frustum-shaped) section 13c that conically tapers in the distal direction, a second cylindrical section 13, and a helical screw fastening section 13e whose basic shape is also cylindrical. The smallest diameter of the conical section 13c is the same as that of the distally adjacent second cylindrical section 13d, and its largest diameter is the same as that of the proximally adjacent second cylindrical section 13b.

The inner part 13 is rotatably movable with respect to the electrode body 11 by means of the helix section 13a through a control on its proximal end (not shown), taking the inner part 13 out of the initial or delivery state shown in FIG. 1A and putting it into the state in which it is used shown in FIG. 1B, the helical screw 15 being extended out of the free end of the lead 11a and fixed by screwing in the patient's body tissue (not shown) against which it is pressed. During the axial rotational displacement of the inner part and the associated extension of the helical screw, the conical section 13c of the inner part passes the flange rings 11b, 11c on the electrode body and the sealing ring 17 held between them and deforms the latter out of the starting shape shown in FIG. 1A into the final shape shown in FIG. 1B. The enlargement of the contact surface or the increase in the axial compressive stress of the sealing ring 17 with the inner part 11 and the compression of the sealing ring gradually increases the resistance exerted by the sealing ring on the further axial displacement of the inner part. In every state, the area proximal of the sealing ring is sealed from the area distal of the sealing ring, that is, in particular, it is sealed from the penetration of body fluid in the implanted state, however the axial movement of the inner part in the initial phase is substantially smoother (and also perceptibly smoother for the operating surgeon) than in the end phase, shortly before the fully extended state of the helical screw 15 is reached.

In the same way as FIG. 1A and FIG. 1B, FIG. 2A and FIG. 2B show another sample embodiment of an implantable lead 20. Its structure is largely the same as that of the first sample embodiment, so that components that correspond to one another are designated with corresponding reference numbers and are not further explained here. The lead 20 differs from the above-described lead 10 in that the inner part 23 has, between the first cylindrical section 23b and the conical or frustum-shaped section 23c, a ring-shaped depression 23f (annular groove) whose cross section has approximately the shape of a circular segment.

This annular groove 23f is positioned and configured so that when the completely extended state of the helical screw 25 is reached, the sealing and resistance element 27 clamped between the flange rings 21b, 21c slides into it, partly reversing its deformation and decompressing it. This leads to a haptically perceivable change in the resistance with which the sealing and resistance element counteracts the extension of the helical screw, thus signaling to the operating surgeon that these means of fixation have reached their fully screwed-out state. A distally arranged screw mechanism does not have the mentioned haptic feedback without the interplay of the system annular groove 23f and sealing and resistance element 27 due to the torsional movement of the inner part 23 and of the electrode body. Consequently, the signaling that the means of fixation have reached the fully extended state, which is otherwise only possible using an X-ray contrast marker, is also feasible or at least verifiable in another way. Moreover, the fact that the sealing ring 27, whose deformation has been partly reversed, is stably resting in the annular groove 23f makes it more difficult, or can even prevent, unintentional withdrawal of the helical screw into the open end of the lead 20, and thus an unintentionally undoing the fixation of the lead to the body tissue.

Figure 3B:
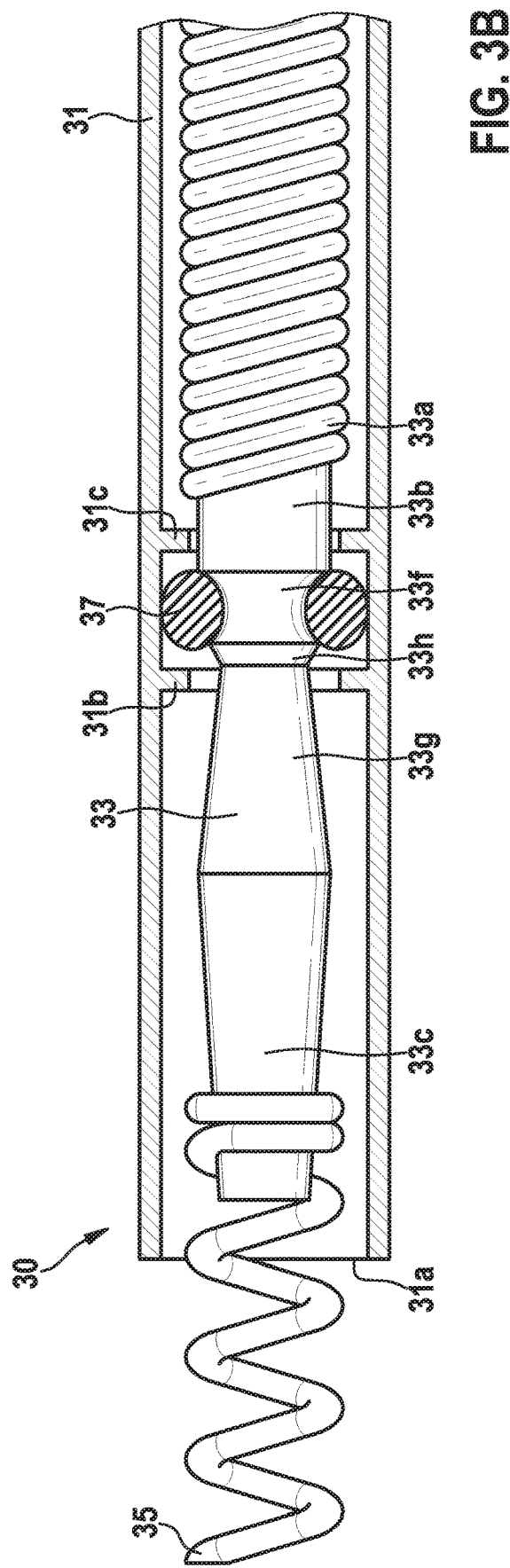

FIGS. 3A and 3B show, in a representation that is once again similar to FIGS. 1A/1B and FIGS. 2A/2B, another sample embodiment of an implantable lead 30. To the extent that their structure corresponds to that of the leads 10 and 20 described further above, the individual parts are provided with corresponding reference numbers and are not described again here.

The lead 30 differs from the leads 10 and 20 in that the inner part 33 has a considerably more complex geometric configuration; here the distal end section 33c of inner part 33 has an uninterrupted slightly conical shape (with a small angle of taper) tapering toward the free end 31a of the lead, followed in the proximal direction by a section 33g that is also slightly conical, however, tapering in the proximal direction, and then a strongly conical widening section 33h, and finally, before the transition to the proximal cylindrical part 33a, an annular groove 33f. The distal, slightly conical section 33c can also be cylindrically shaped.

The essential effects of this structure of the inner part are as follows: If, in the transition from the initial state shown in FIG. 3A into the final state shown in FIG. 3B (the implanted state), the section 33g of the inner part 33, this section slightly tapering in the proximal direction, passes the sealing and resistance element 37, the latter can gradually expand, so that the displacement of the inner part with respect to the electrode body 31 becomes easier the further the helical screw 35 is extended, all the way to the point of transition to the widening section 33h. There the sealing and resistance element 37 undergoes an abrupt compression, which manifests itself as a perceptible increase in resistance, before the sealing and resistance element 37 finally slides into the annular groove 33f and once again somewhat expands.

This configuration allows even clearer perception of when the final state of extension of the helical screw (the means of fixation) 35 is approaching, and when it has been reached. As in the case of the lead 20, the "latching" of the sealing and resistance element 37 into the annular groove 33f of the inner part also causes a largely automatic locking of the inner part, and thus of the helical screw, with respect to the electrode body in the extended state. In addition, should this first braking action or locking nevertheless be overcome, a further unintentional withdrawal of the means of fixation back into the lead, or their being pressed back into the lead (for example, by the action of external forces) is counteracted by increasing resistance due to the reverse conical shape of section 33g of the inner part.

Moreover, this reverse conical (i.e., tapering in the proximal direction) section 33g has the effect that the inner part 33 can extend out of the electrode body so to speak "by itself", that is without the application of substantial effort, and thus the helical screw also largely automatically screws into the body tissue to which the lead is to be fixed.

If the section 33c arranged distal of section 33g is designed to be slightly tapering toward the free end and if this section also passes through the sealing and resistance element 37 when the inner part undergoes rotational displacement with respect to the electrode body, there is an additional step of the extension movement, namely a first step with gradually somewhat increasing resistance before the reversal point of the taper is reached and the second movement phase with gradually decreasing resistance follows.

It follows from the above that a complex structure of the inner part with multiple conical sections and/or annular grooves can largely achieve desired axial resistance behavior when the means of fixation extend out of an inventive lead.

Only as an example without more exact description, one more configuration will be mentioned here, in which an annular groove is provided at a place in the inner part such that the sealing and resistance element on the electrode body rests in it when the inner part is in its completely retracted state (that is, in the delivery state of the lead). This securely prevents the inner part being displaced with respect to the electrode body already before the implantation process, that is, for example, during transport, and the means of fixation unintentionally exiting from the end of the lead.

Figure 4:
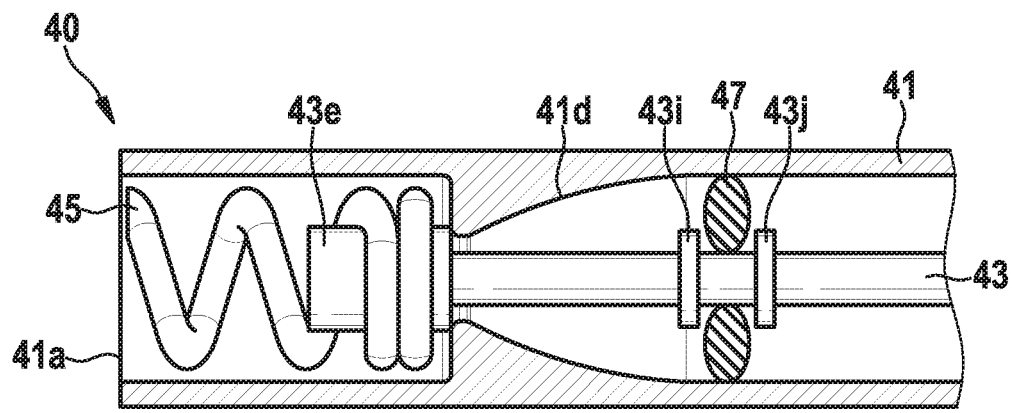
FIG. 4 shows a schematic longitudinal section of an implantable lead according to a fourth embodiment of the invention with its means of fixation pulled back.

FIG. 4 is a schematic longitudinal section showing another sample embodiment of an implantable lead 40, in which the assignment of essential parts or sections is the opposite of that in the above-described embodiments according to FIGS. 1A/1B through 3A/3B. Once again, components that are the same or functionally similar are designated with reference numbers that are adapted to the FIGS. 1A/1B through 3A/3B, and are not described again here in detail.

In the lead 40, a sealing ring (sealing and resistance element) 47 made of compressible deformable material (for instance, a PU synthetic) is put between two flange rings 43i, 43j on the inner part 43, which has an uninterrupted cylindrical shape here, except for the distal fastening section 43e for a helical screw 45. However, in this lead 40, the electrode body 41 has a tapering section 41d in which the inside diameter of the electrode body progressively decreases in the distal direction. When the inner part 43 is rotatably displaced with respect to the electrode body 41 causing the extension of the helical screw 45, the sealing and resistance element 47 passes through this section 41d with progressively decreasing diameter, is progressively deformed and compressed in the process, and as a result of this counteracts the further movement with a progressively increasing resistance.

Figure 5:
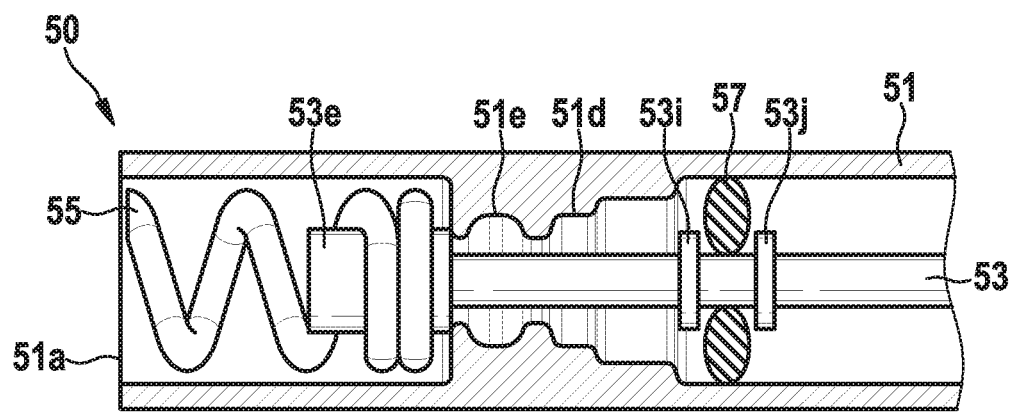
FIG. 5 shows a schematic longitudinal section of an implantable lead according to a fifth embodiment of the invention with its means of fixation pulled back.

FIG. 5 shows another example of a lead 50 whose structure largely corresponds to that of the lead 40 in FIG. 4 and whose components consequently have reference numbers adapted to FIG. 4. The lead 50 differs from the lead 40 in another geometric configuration of the electrode body 51. Here, the latter comprises a tapering section 51d whose inside diameter decreases in steps followed in the distal direction by an annular groove 51e whose cross section has approximately the shape of a circular segment.

When the stepped section 51d passes through the inner part 53 with the sealing and resistance element 57 fixed to it, it increases the compression and deformation of the sealing and resistance element in a stepwise manner, which increases the resistance counteracting further movement, also in a stepwise manner. These resistance steps are perceptible for the operating surgeon, and each of them signals to him one step in the extension of the helical screw 55 out of the end of the lead 51a. Similar to the case with the lead 20 according to FIGS. 2A/2B, at the end of the extension movement of the helical screw the sealing and resistance element slides into the annular groove 51e and re-expands somewhat, which causes an abrupt reduction in resistance and signals to the operating surgeon the end of the extension and fixation process.

Figure 6:
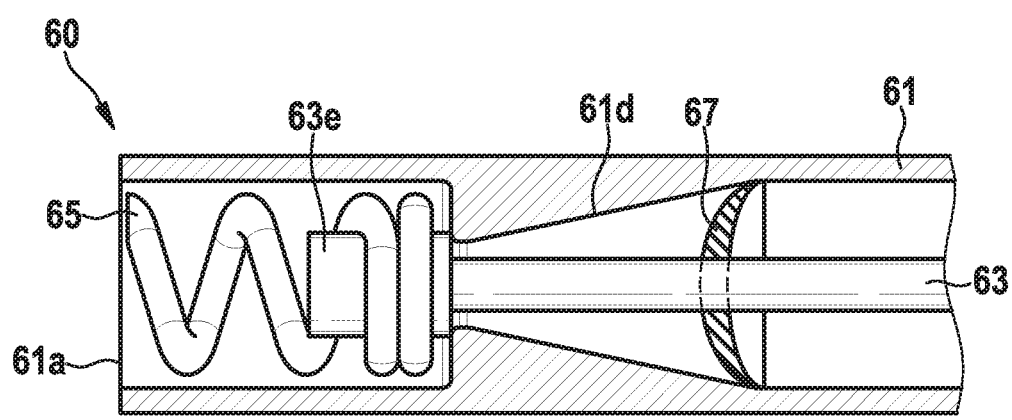
FIG. 6 shows a schematic longitudinal section of an implantable lead according to a sixth embodiment of the invention with its means of fixation pulled back.

FIG. 6 shows another example of an implantable lead 60 whose structure largely corresponds to that of lead 40 according to FIG. 4, so that here also corresponding reference numbers have been assigned and explanations given further above have not been repeated.

An essential difference from the lead 40 is that the tapering section 61d on the inner periphery of the electrode body 61 is conical, i.e., frustum-shaped. Another essential difference is that the sealing and resistance element 67 on the inner part is in the form of a basket-like, softly elastic element without substantial compressibility, made of a silicone material, for instance. As the inner part 63 is progressively moved toward the open end 61a of the lead, the sealing and resistance element 67 is increasingly bent together toward the longitudinal axis of the inner part 63, which increases its friction surface with respect to the inner wall of the electrode body and the contact pressure against this inner wall, which counteracts the further movement with an increasing frictional resistance.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

We claim:

1. An implantable lead comprising:
a hollow electrode body with a free end and, arranged in the electrode body near its free end, an inner part that is axially or rotatably movable with respect to it and that has, adjacent to the free end of the electrode body, an end on which there are means of fixation that can be extended out of the free end of the electrode body by axially displacing the inner part, these means of fixation being intended to fix the lead to body tissues in the implanted state, the inner periphery of the electrode body having an elastically deformable, peripheral, especially ring-shaped or ring segment-shaped, sealing and resistance element fixed to it, and the outer periphery of the inner part having a section whose diameter changes in the axial direction by decreasing toward the free end of the electrode body, this section being placed with respect to the sealing and resistance element so that this section passes the sealing and resistance element when the inner part is axially displaced, the sealing and resistance element being increasingly deformed during the axial displacement of the inner part and counteracting the movement of the inner part and thus the extension of the means of fixation with increasing resistance.

2. The implantable lead according to claim 1, wherein h inner part is held so that it is rotatably movable in the electrode body, in such a way that the means of fixation can be extended out of the free end of the electrode body by superimposed axial displacement and rotation.

3. The implantable lead according to claim 2, wherein the means of fixation are in the form of a helical screw.

4. The implantable lead according to claim 3, wherein a screw mechanism arranged at the distal end of the electrode body is realized by an advancing element that interacts with a helical screw.

5. The implantable lead according to claim 1, wherein the section with changing diameter on the inner part is followed, at least on one side in the axial direction of the lead, by a section of constant diameter whose diameter is equal to the smallest or the largest diameter of the section with decreasing diameter.

6. The implantable lead according to claim 5, wherein at least one section of the inner part or the inner wall of the electrode body has a coating on it with a predetermined coefficient of friction with respect to the sealing and resistance element for selective increase or decrease of the resistance counteracting the axial displacement or rotational displacement of the inner part.

7. The implantable lead according to claim 6, wherein various sections of the inner part or the inner wall of the electrode body have coatings on them with different coefficients of friction with respect to the sealing and resistance element.

8. The implantable lead according to claim 1, wherein the sealing and resistance element is a ring made of compressible material, this ring being clamped on the inner periphery of the electrode body so that it is increasingly compressed as the section with the changing diameter of the inner part passes while the means of fixation are being extended.

9. The implantable lead according to claim 8, wherein the sealing and resistance element has a silicone or polyurethane material.

10. The implantable lead according to claim 1, in the form of an electrode lead for connection to an electromedical device, with at least one electrode pole and at least one electrical lead.

11. The implantable lead according to claim 1, in the form of a catheter lead.

12. The implantable lead according to claim 1, wherein the sealing and resistance element is made of elastic material that is clamped on the inner periphery of the electrode body in, such a way and has such a geometric configuration that it is increasingly deformed and deformed with increasing resistance as it passes the section with changing diameter of the inner part to extend the means of fixation.

13. The implantable lead according to claim 1, wherein the section with changing diameter has, arranged at or near one end of it, an annular groove section, into which the sealing and resistance element slides as the means of fixation are extended and/or pulled back in, partly reversing the deformation of the sealing and resistance element, and counteracting tither axial movement of the inner part with respect to the electrode body with an abruptly increased resistance.

14. The implantable lead according to claim 1, wherein the section with changing diameter has a conical shape.

15. The implantable lead according to claim 1, wherein the section with changing diameter has a surface that tapers in steps or in the form of an arch.

16. The implantable lead according to claim 1 wherein the inner part has multiple sections with changing diameter, in particular with diameter that decreases in opposite directions and/or with a different angle of taper.

17. An implantable lead comprising:
a hollow electrode body with a free end and, arranged in the electrode body near its free end, an inner part that is axially or rotatably movable with respect to it and that has, adjacent to the free end of the electrode body, an end on which there are means of fixation that can be extended out of the free end of the electrode body by axially displacing the inner part, these means of fixation being intended to fix the lead to body tissues in the implanted state, the outer periphery of the inner part having an elastically deformable ring-shaped or ring segment-shaped sealing and resistance element fixed to it, and the inner periphery of the electrode body having a section whose diameter changes in the axial direction by decreasing toward the free end of the electrode body, this section being placed with respect to the sealing and resistance element so that the sealing and resistance element passes this section when the inner part is axially displaced, the sealing and resistance element being increasingly deformed during the axial displacement of the inner part and counteracting the movement of the inner part and thus the extension of the means of fixation with increasing resistance.

18. The implantable lead according to claim 17, wherein the sealing and resistance element is a ring made of compressible material, this ring being clamped on the outer periphery of the inner part so that it is increasingly compressed as the section with the changing diameter of the electrode body passes while the means of fixation are being extended.

19. The implantable lead according to claim 17, wherein the sealing and resistance element is made of elastic material that is clamped on the outer periphery of the inner part in such a way and has such a geometric configuration that it is increasingly deformed and deformed with increasing resistance as it passes the section with changing diameter of the electrode body to extend the means of fixation.

20. The implantable lead according to claim 17 wherein the section with changing diameter on the electrode body is followed, at least on one side in the axial direction of the lead, by a section of constant diameter whose diameter is equal to the smallest or the largest diameter of the section with decreasing diameter.

21. The implantable lead according to claim 17, wherein the electrode body has multiple sections with changing diameter, in particular with diameter that decreases in opposite directions and/or with a different angle of taper.

* * * * *